United States Patent [19]

Tycer et al.

[11] Patent Number: 4,981,578

[45] Date of Patent: Jan. 1, 1991

[54] BF$_3$ REMOVAL FROM BF$_3$ CATALYZED OLEFIN OLIGOMER

[75] Inventors: Lindsay T. Tycer, Denham Springs; Everett M. Marlett, Baton Rouge, both of La.

[73] Assignee: Ethyl Corporation, Richmond, Va.

[21] Appl. No.: 447,168

[22] Filed: Dec. 7, 1989

[51] Int. Cl.$^5$ .............................................. C10G 17/02
[52] U.S. Cl. .................................. 208/262.1; 585/525; 585/833
[58] Field of Search ..................... 208/262.1, 280, 283; 585/465, 525, 820, 833, 935, 823, 824

[56] References Cited

U.S. PATENT DOCUMENTS

| | | | |
|---|---|---|---|
| 2,628,991 | 2/1953 | Schneider et al. | 585/525 |
| 3,331,881 | 7/1967 | Nixon et al. | 208/262.1 |
| 4,239,930 | 12/1980 | Allphin et al. | 585/525 X |
| 4,263,467 | 4/1981 | Madgavkar et al. | 585/525 |
| 4,384,162 | 5/1983 | Vogel et al. | 208/262.1 |
| 4,433,197 | 2/1984 | Vogel et al. | 208/262.1 |

*Primary Examiner*—Anthony McFarlane
*Assistant Examiner*—William Diemler
*Attorney, Agent, or Firm*—Joseph D. Odenweller; David M. Bunnell

[57] ABSTRACT

BF$_3$ is removed from a promoted BF$_3$ catalyzed olefin oligomer reaction product by contacting the reaction product with either solid or aqueous KF to form a solid KBF$_4$ precipitate. Solid NaF or NH$_4$F can also be used.

19 Claims, No Drawings

BF$_3$ REMOVAL FROM BF$_3$ CATALYZED OLEFIN OLIGOMER

BACKGROUND OF THE INVENTION

Alpha-olefin oligomers and their use as hydraulic fluids and synthetic lubricants (synlubes) are well known. U.S. Pat. No.2,937,129 reports the oligomerization of C$_{5-14}$ α-olefins using a dialkyl peroxide catalyst to make a synlube. U.S. Pat No. 3,113,167 describes an α-olefin oligomer process using a titanium halide and an aluminum compound as the oligomerization catalyst.

The preferred catalysts for making α-olefin oligomers are Friedel-Crafts catalysts such as boron trifluoride (BF$_3$) as disclosed in U.S. Pat. No. 3,149,178. Optimum properties are obtained starting with 1-decene although mixtures of α-olefins have been used, cf. U.S. Pat. No. 3,330,883.

The preferred Friedel-Crafts catalyst is BF$_3$. Pure BF$_3$ is not an effective oligomerization catalyst. A small amount of polar compound is necessary as a promoter. U.S. Pat. No. 3,382,291 describes the use of alcohol promoters such as decanol. Other reported promoters are mordenite (hydrogen form), water, phosphoric acid, fatty acids (e.g. valeric acid), ketones, organic esters, ethers, polyhydric alcohols, silica gel and the like.

The most common catalyst, BF$_3$, can present a disposal problem. Various methods have been devised for removing BF$_3$ from an oligomerization reaction to achieve an environmentally acceptable result. Vogel et al. U.S. Pat. No. 4,454,366 and U.S. Pat. No. 4,384,162 describe the use of polyvinyl alcohol to remove BF$_3$ from an oligomerization reaction. Vogel et al. U.S. Pat. No. 4,433,197 contacts the reaction product with silica to remove the BF$_3$. Morganson et al. U.S. Pat. No.4,429,177 and Madgavkar et al. U.S. Pat. No. 4,213,001 and U.S. Pat. No. 4,308,414 use silica as an absorbant for BF$_3$ in an oligomerization process. Madgavkar et al. U.S. Pat. No. 4,394,296 describe the use of wet silica as a co-catalyst with BF$_3$ in an oligomer process. The silica can be filtered off and recycled as the catalyst. Madgavkar et al. U.S. Pat. No. 4,263,467 remove BF$_3$ by trickling the reaction product over an inert metallic or ceramic bed whereby the BF$_3$ is said to evaporate and can be recovered.

From this it can be seen that a great deal of effort has gone into developing a method for removing BF$_3$ from an olefin oligomerization process in an environmentally safe manner.

SUMMARY

According to the present invention, BF$_3$ is removed from an olefin oligomer reaction product containing BF$_3$ by contacting the oligomer with potassium fluoride (KF) and/or sodium fluoride (NaF) and/or ammonium fluoride (NH$_4$F) whereby BF$_3$ reacts to form potassium fluoroborate (KBF$_4$) and/or sodium fluoroborate (NaBF$_4$) and/or ammonium fluoroborate (NH$_4$BF$_4$) which are insoluble in the oligomer and can be removed by conventional means such as decantation or filtration.

DESCRIPTION OF THE PREFERRED EMBODIMENTS

A preferred embodiment of the invention is a method of removing BF$_3$ from a promoted BF$_3$ catalyzed olefin oligomer reaction product, said process comprising contacting said reaction product with solid alkali metal or ammonium fluoride or an aqueous potassium fluoride solution to cause said BF$_3$ to precipitate as a fluoroborate salt and separating said fluoroborate salt from said reaction product.

Methods of conducting a BF$_3$ catalyzed oligomerization process are well-known. In one mode, BF$_3$ is merely bubbled through the α-olefin reaction mixture containing a promoter during the oligomerization. In a preferred mode, the process is conducted under BF$_3$ pressure. A useful pressure is about 1-100 psig, preferably 5-50 psig and more preferably about 10-20 psig.

Any of the known promoters for BF$_3$ can be used such as water, alcohol (e.g. methanol, ethanol, n-propanol, isopropanol, n-butanol, isobutanol, n-hexanol, 2-ethyl hexanol, n-decanol, n-dodecanol and the like including mixtures thereof), fatty acids (e.g. valeric, caproic and the like), organic esters (e.g. butyl acetate, methyl valerate, ethyl octanoate, and the like), ketones (e.g. methyl ethyl ketone, methyl isobutyl ketone, and the like), ethers (e.g. dibutyl ether, tetrahydrofuran, dioxane and the like), alkoxylated alcohols (e.g. 2-ethoxyethanol, and the like), polyhydric alcohols (e.g. glycol, glycerol and the like), inorganic acids (e.g. phosphoric and the like), silica, zeolites and the like.

The preferred promoters having these properties are water and alcohols containing about 1-8 carbon atoms such as methanol, ethanol, isopropanol, n-propanol, n-butanol, isobutanol, n-hexanol and n-octanol. The more preferred promoters are alcohols containing about 2-5 carbon atoms. The most preferred promoter is n-butanol.

The amount of promoter should be an amount that causes the BF$_3$ to act as an oligomerization catalyst. This is referred to as a promoter amount. A useful range is about 0.1-2.0 weight percent of the α-olefin.

Alpha-olefins useful in the process are those containing about 8-12 carbon atoms such as 1-octene, 1-decene, 1-dodecene and the like including mixtures thereof. The most preferred α-olefin is 1-decene or an olefin mixture containing mainly, for example, at least 75 weight percent 1-decene.

The preferred reaction temperature is about 20-50° C. and more preferably about 25-40° C. Superior results have been achieved at about 30° C. Lower temperatures will increase the amount of higher oligomers but at the cost of a slower reaction rate. High temperatures give a fast reaction rate but increased yield of dimer.

The oligomerization is usually conducted until the monomer content of the reaction mixture drops below about 5 weight percent, more preferably below about 2 weight percent. After the oligomerization reaction has proceeded to the desired extent, the oligomer reaction mixture is contacted with either solid KF or with an aqueous KF solution.

When using solid KF, at least a stoichiometric amount (based on the reaction BF$_3$+KF→KBF$_4$) of KF is contacted with the BF$_3$-containing oligomer. The solid KF can be either added to the oligomer and stirred for a period of about one minute to four hours or longer and then separated from the oligomer by solid/liquid separation means such as filtration or decantation. The KBF$_4$ is insoluble and remains with the solids.

In another mode of operation, the oligomer product containing the BF$_3$ is passed through a bed of particulate KF. The amount of KF in the bed should be at least a stoichiometric amount based on the BF$_3$ content of the oligomer. Preferably an excess amount of KF is used, e.g. 1.5-100 times the stoichiometric amount, to prevent BF$_3$ breakthrough. The contact time of the oligomer with the KF bed should be long enough to permit all or most of the BF$_3$ to react with the KF. A contact time of about 30 seconds to four hours is a useful range in which to test. The KBF$_4$ which forms has been found in experiments to remain with the particulate KF.

In both of the above modes, the promoter will remain in the oligomer unless it is insoluble in the oligomer. The promoter, if water soluble, can be washed out with water. Alternatively, the promoter can be distilled out either as a single fraction or combined with unreacted olefin monomer and possibly dimer. These can be recycled to a subsequent reaction.

In another embodiment the oligomer product containing BF$_3$ and promoter is contacted with an aqueous KF solution. The KF concentration can range from about one weight percent up to its solubility limit, about 48 weight percent KF. Since KBF$_4$ is reported to have a solubility in cold water of only 0.44 weight percent, most of the BF$_3$ will precipitate as KBF$_4$. In order to minimize the amount of KBF$_4$ remaining in water solution, it is preferred that the aqueous KF solution contain at least 10 weight percent KF and more preferably at least 25 weight percent KF. Most preferably the aqueous KF solution is about 35 weight percent KF up to a KF saturated solution.

The amount of aqueous KF should provide at least a stoichiometric amount of KF, i.e. at least one mole KF per mole BF$_3$ in the oligomer unless incomplete removal of the BF$_3$ is acceptable. A useful range in which to operate is about 0.9–100 mole KF/mole BF$_3$ and more preferably about 1–10 moles KF per mole BF$_3$ and most preferably about 1.0–1.1 moles KF/mole BF$_3$.

The aqueous KF should be contacted with the oligomer for a time sufficient to react with the BF$_3$. A period of about one minute to four hours is usually satisfactory. A solid precipitate forms. The aqueous phase can then be separated. Part of the solids will generally separate with the aqueous phase. Solids remaining in the organic phase can be removed by filtration.

When aqueous KF is used, at least part of any water soluble promoter, such as the lower alcohols, will also be extracted into the aqueous phase.

In a highly preferred embodiment, the oligomer reaction mixture containing BF$_3$ is first contacted with aqueous KF to remove most of the boron. After separating the aqueous phase, the organic phase, with or without filtration, is then passed through a bed of particulate KF and/or NaF and/or NH$_4$F in a polishing operation. This has been shown to reduce the boron concentration in the oligomer to extremely low levels.

A further benefit that has been observed is a reduction in color of the oligomer product. Olefin oligomers made using alcohol-promoted BF$_3$ frequently have a reddish-brown hue. After treatment with KF, the oligomer has been observed to turn white.

Another method of removing the BF$_3$ from the oligomer is to water-wash the oligomer to remove the BF$_3$ into an aqueous wash phase. The aqueous phase is separated and at least a stoichiometric amount of KF, based on BF$_3$, is added to the aqueous wash and stirred until all or most of the BF$_3$ precipitates as KBF$_4$. This can be removed by filtration.

The KBF$_4$ recovered by the present process can be used to regenerate BF$_3$. Heating KBF$_4$ to high temperatures causes it to decompose to KF and BF$_3$. Alternatively, it can be mixed with concentrated H$_2$SO$_4$ and heated to drive off HF and BF$_3$.

In another embodiment, particulate NaF and/or NH$_4$F can be used to treat the BF$_3$-containing oligomer in place of or in combination with KF. Sodium fluoride and NH$_4$F form NaBF$_4$ and NH$_4$BF$_4$ which are insoluble in the oligomer so can be used just like the particulate KF. Sodium fluoroborate and NH$_4$BF$_4$ are very soluble in water so it is preferred not to use aqueous NaF or NH$_4$F to treat the oligomer unless a means of disposing of the resulting aqueous NaBF$_4$ or NH$_4$BF$_4$ is available. One such means would be to evaporate off all the water and then add concentrated sulfuric acid and heat to drive off BF$_3$ and HF which are both useful products.

In another embodiment which is considered equivalent to those already described, KHF$_2$ and/or NaHF$_2$ and/or NH$_4$F·HF are used in place of KF and/or NaF and/or NH$_4$F to reduce cost. In this embodiment an equal mole amount of KOH and/or NaOH and/or NH$_4$OH is added to convert the KHF$_2$ and/or NaHF$_2$ and/or NH$_4$F·HF to KF and/or NaF and/or NH$_4$F as the case may be.

The following examples show how the process can be carried out and the results that can be achieved.

EXAMPLE 1

In a Nalgene ® bottle was placed 0.5 parts by weight of powdered KF and 8 parts of 1-decene oligomer containing 0.32 weight percent boron as BF$_3$ (3200 ppm boron) and a small amount of n-butanol promoter. The bottle was shaken for two minutes and then placed in an ultrasonic bath for 30 minutes and again shaken for an additional 2 minutes. The oligomer turned from red in color to white. The liquid was then filtered and the filtrate analyzed for boron. The analysis showed less than 1 ppm boron indicating that the BF$_3$ had been substantially all removed by contact with KF.

EXAMPLE 2

In a Nalgene ® bottle was placed 10 parts by weight of a 1-decene oligomer containing 0.51 weight percent BF$_3$ (820 ppm boron) and 0.1 parts of a saturated (48 weight percent) aqueous KF solution.

In a second Nalgene ® bottle was placed 10 parts of the same 1-decene oligomer and 0.1 parts deionized water.

Both bottles were shaken and the organic phases were separated from the aqueous phases. A solid precipitated from the aqueous KF-extracted mixture and was removed by filtration. Both extracted oligomers were analyzed for boron. The results were as follows.

|  | Boron (ppm) |
| --- | --- |
| Initial oligomer | 820 |
| Water-extracted oligomer | 140 |
| KF/water-extracted oligomer | 63 |

This shows that the aqueous KF extraction is much more efficient than water extraction in removing BF$_3$. The solids which separated from the KF/water-treated oligomer were analyzed by x-ray powder diffraction and found to be KBF$_4$.

EXAMPLE 3

A packed column was prepared containing a 2-inch bed of particulate KF. The oligomer from Example 2 that had been extracted with KF/water was passed down through the KF bed and then analyzed for boron. The results were as follows.

|  | Boron (ppm) |
| --- | --- |
| Initial oligomer | 820 |
| KF/water-extracted oligomer | 63 |
| After KF column | 6 |

These results show that passing the oligomer containing $BF_3$ through a particulate KF bed practically eliminates $BF_3$ from the oligomer. It is not necessary to initially extract the oligomer with aqueous KF. The oligomer containing $BF_3$ can be transferred directly from the oligomerization reaction to the particulate KF column for removal of $BF_3$.

Following $BF_3$ removal, the olefin oligomer is worked-up in a conventional manner usually including distillation to remove monomer and dimer (and promoter if present) followed by hydrogenation to form a saturated olefin oligomer. Such saturated oligomers have many uses such as in lubricating oils and greases, hydraulic fluids, dielectric transformer oil and the like.

We claim:

1. A method of removing $BF_3$ from a promoted $BF_3$ catalyzed olefin oligomer liquid reaction product, said process comprising contacting said reaction product with a composition consisting essentially of solid alkali metal fluoride or ammonium fluoride or an aqueous potassium fluoride solution to cause said $BF_3$ to precipitate as the fluoroborates and separating said fluoroborates from said reaction product.

2. A process of claim 1 wherein the $BF_3$ catalyst is promoted with a $C_{1-12}$ alcohol.

3. A process of claim 1 wherein said olefin oligomer liquid reaction product is passed through a bed of particulate NaF and/or KF and/or $NH_4F$ whereby the $BF_3$ catalyst reacts with the NaF and/or KF and/or $NH_4F$ to form $NaBF_4$ and/or $KBF_4$ and/or $NH_4BF_4$ which is removed from said reaction product and remains in said bed.

4. A process of claim 3 wherein said particulate is KF.

5. A process of claim 2 wherein said promoted $BF_3$ is n-butanol promoted $BF_3$.

6. A process of claim 3 wherein said promoted $BF_3$ is a $C_{1-12}$ alcohol promoted $BF_3$.

7. A process of claim 6 wherein said alcohol is n-butanol.

8. A process of claim 1 wherein said olefin is mainly 1-decene.

9. A process of claim 8 wherein said promoted $BF_3$ is a $C_{1-12}$ alcohol promoted $BF_3$.

10. A process of claim 9 wherein said olefin oligomer liquid reaction product is passed through a bed of particulate NaF and/or KF and/or $NH_4F$ whereby the $BF_3$ catalyst reacts with the NaF and/or KF and/or $NH_4F$ to form $NaBF_4$ and/or $KBF_4$ and/or $NH_4BF_4$ which is removed from said reaction product and remains in said bed.

11. A method of removing $BF_3$ from a promoted $BF_3$ catalyzed olefin oligomer reaction product, said process comprising (a) washing said reaction product with water to extract said $BF_3$ into the aqueous phase, (b) separating the aqueous phase, (c) adding KF to the separated aqueous phase in an amount sufficient to react with the $BF_3$ to form $KBF_4$ and (d) separating said $KBF_4$ from said aqueous phase.

12. A process of claim 11 wherein after separating the aqueous phase, the remaining organic phase is passed through a bed of particulate NaF and/or KF and/or $NH_4F$ whereby the $BF_3$ content of the organic phase is further decreased.

13. A process for removing $BF_3$ from an olefin oligomer liquid containing $BF_3$, said process comprising passing said olefin oligomer through a bed consisting essentially of particulate KF.

14. A process of removing $BF_3$ from a promoted $BF_3$ catalyzed olefin oligomer reaction product said process comprising first contacting said reaction product with aqueous KF to remove a portion of the $BF_3$ catalyst and then passing the remaining organic phase through a bed of particulate NaF and/or KF and/or $NH_4F$ to further lower the $BF_3$ content of the organic phase.

15. A process of claim 14 wherein said olefin is mainly 1-decene and said promoted $BF_3$ is a $C_{1-12}$ alcohol promoted $BF_3$.

16. A process of claim 15 wherein said alcohol is n-butanol.

17. A process of claim 14 wherein said particulate is KF.

18. A process of claim 14 wherein said promoter is a $C_{1-12}$ alcohol.

19. A process of claim 18 wherein said alcohol is n-butanol.

* * * * *